(12) United States Patent
Ueda et al.

(10) Patent No.: US 12,108,892 B2
(45) Date of Patent: Oct. 8, 2024

(54) INFORMATION PROCESSING APPARATUS

(71) Applicant: NTT DOCOMO, INC., Chiyoda-ku (JP)

(72) Inventors: Kensuke Ueda, Chiyoda-ku (JP); Nobutaka Matsushima, Chiyoda-ku (JP)

(73) Assignee: NTT DOCOMO, INC., Chiyoda-ku (JP)

( * ) Notice: Subject to any disclaimer, the term of this patent is extended or adjusted under 35 U.S.C. 154(b) by 372 days.

(21) Appl. No.: 17/769,927

(22) PCT Filed: Nov. 11, 2020

(86) PCT No.: PCT/JP2020/042073
§ 371 (c)(1),
(2) Date: Apr. 18, 2022

(87) PCT Pub. No.: WO2021/095767
PCT Pub. Date: May 20, 2021

(65) Prior Publication Data
US 2022/0386797 A1     Dec. 8, 2022

(30) Foreign Application Priority Data

Nov. 15, 2019  (JP) ................................ 2019-206663

(51) Int. Cl.
*G06V 40/10*   (2022.01)
*A47G 23/10*   (2006.01)
(Continued)

(52) U.S. Cl.
CPC ............... *A47G 23/10* (2013.01); *G06T 7/20* (2013.01); *G06V 10/761* (2022.01); *G06V 20/46* (2022.01);
(Continued)

(58) Field of Classification Search
CPC . A47G 23/10; G06T 7/20; G06T 2207/10016; G06T 2207/30128;
(Continued)

(56) References Cited

U.S. PATENT DOCUMENTS

| 2016/0012749 | A1* | 1/2016 | Connor | ..................... | A61B 5/24 600/27 |
| 2020/0152312 | A1* | 5/2020 | Connor | .................. | G06V 20/20 |
| 2023/0335253 | A1* | 10/2023 | Connor | ................... | G06F 3/013 |

OTHER PUBLICATIONS

International Search Report issued Dec. 28, 2020 in PCT/JP2020/042073 filed on Nov. 11, 2020, 2 pages.
(Continued)

*Primary Examiner* — Chuong A Ngo
(74) *Attorney, Agent, or Firm* — Oblon, McClelland, Maier & Neustadt, L.L.P.

(57) ABSTRACT

An information processing apparatus includes, when a first determiner determines the amount of food or beverage in a platter being decreased, a second determiner to determine whether food or beverage on the platter was consumed by one person of multiple people, or the food or beverage was moved onto one small plate of small plates, a consumption information generator to generate, when the food or beverage on the platter was consumed by the one person, consumption information in which an amount of food or beverage consumed by the one person, the one person, and the type of the food or beverage are associated with each other, and an estimator to increase, when the food or beverage was moved to one small plate, the amount of food or beverage on the one small plate by an amount of decrease in the food or beverage in the platter.

6 Claims, 10 Drawing Sheets

(51) Int. Cl.
    *G06T 7/20*           (2017.01)
    *G06V 10/74*         (2022.01)
    *G06V 20/40*         (2022.01)
    *G06V 20/68*         (2022.01)
    *G16H 20/60*         (2018.01)

(52) U.S. Cl.
    CPC .............. *G06V 20/68* (2022.01); *G06V 40/10* (2022.01); *G16H 20/60* (2018.01); *G06T 2207/10016* (2013.01)

(58) Field of Classification Search
    CPC . G06T 2207/30196; G06T 2207/30232; G06T 2207/30241; G06T 2207/30242; G06T 7/246; G06V 10/761; G06V 20/46; G06V 20/68; G06V 40/10; G06V 20/52; G06V 40/28; G16H 20/60; G16H 30/40
    See application file for complete search history.

(56) References Cited

OTHER PUBLICATIONS

Otsuka et al., "Adaptive tabletop dish recommendation system by the recognition of realtime dining activity of multiple participants", IPSJ SIG Technical Report, vol. 2011-GN-78 No. 8, Jan. 21, 2011, 7 pages (with English Abstract).

\* cited by examiner

| SMALL EXTRA PLATE ID | PERSON ID |
|---|---|
| SP_1 | U_1 |
| SP_2 | U_2 |

FIG. 8

| PERSON IDENTIFICATION INFORMATION | AMOUNT OF FOOD | FOOD IDENTIFICATION INFORMATION | TIME INFORMATION | CONSUMPTION MODE INFORMATION | |
|---|---|---|---|---|---|
| U_1 | xx CALORIES | FT_1 | 12:00:01 | FROM SMALL EXTRA PLATE SP_1 | ─ TI_1 |
| U_2 | yy CALORIES | FT_2 | 12:00:03 | FROM SMALL EXTRA PLATE SP_1 | ─ TI_2 |
| ... | ... | ... | ... | ... | |
| U_1 | zz CALORIES | FT_1 | 12:20:00 | FROM PLATTER CP | ─ TI_M |

INFORMATION PROCESSING APPARATUS

TECHNICAL FIELD

The present invention relates to an information processing apparatus.

BACKGROUND ART

Recently, with increase in health consciousness, more people are recording amounts of their dietary consumption. Therefore, to facilitate the recording of amounts of dietary consumption, there have been proposed services for recording amounts of dietary consumption. For example, Non-Patent Document 1 discloses a technique of dividing an image, which is obtained by photographically capturing a dining table in a situation in which multiple people consume food served on a platter, into a plurality of regions, determining whether food is consumed in each region, and recording amounts of dietary consumption of a person corresponding to a region if consumed.

RELATED ART DOCUMENT

Non-Patent Document

Non-Patent Document 1: Yuichiro Otsuka, Yuriko Kourai, and Tomoo Inoue, "Adaptive tabletop dish recommendation system by the recognition of realtime dining activity of multiple participants", IPSJ SIG Technical Report, Vol. 2011-GN-78 No. 8, 2011/1/21

SUMMARY OF THE INVENTION

Problem to be Solved by the Invention

However, in actual dining, some people may move food from a platter to a small extra plate to eat the food from the small extra plate. Conventionally, when an amount of food served on a platter decreases, it is judged that the food has been eaten, even if the food was not eaten, but was instead moved onto a small extra plate; therefore, an amount of dietary consumption could not be accurately judged.

To solve the above problem, an information processing apparatus according to a preferred mode of the present invention includes an acquirer configured to acquire video image information indicative of a video image obtained by photographically capturing a table, on which a vessel of a first type to serve food and beverage to be consumed by multiple people, and a plurality of vessels of a second type in each of which a portion of the food or beverage is to be served are arranged, and the multiple people, an identification information generator configured to generate, based on the video image information, first identification information for identifying each of the multiple people, second identification information for identifying each of the vessel of the first type and the plurality of vessels of the second type, and third identification information for identifying the type of food or beverage, an estimator configured to estimate, based on the video image information, an amount of the food or beverage served in each vessel of the first type and the plurality of vessels of the second type, a first determiner configured to determine, based on the video image information, whether an amount of the food or beverage served in the vessel of the first type at a point in time of a determination is decreased compared to an amount of the food or beverage served in the vessel of the first type at a point in time that is a predetermined period prior to the point in time of the determination, a second determiner configured to, when a result of a determination by the first determiner is affirmative, determine, based on the video image information, whether the food or beverage served on the vessel of the first type was consumed by one person of the multiple people, or whether food or beverage was moved into one vessel of the plurality of vessels of the second type, and a consumption information generator configured to, when a result of a determination by the second determiner indicates that food or beverage served in the vessel of the first type was consumed by the one person, generate consumption information in which amount of food or beverage consumed by the one person, the one person, and the type of food or beverage are associated with each other, and the estimator is configured to, when the result of the determination by the second determiner indicates that food or beverage was moved into the one vessel, increase the amount of the food or beverage served in the one vessel of the second type by amount of decrease in food or beverage served in the vessel of the first type.

Effect of the Invention

According to the present invention, it is possible to accurately judge an amount of dietary consumption of a person.

BRIEF DESCRIPTION OF THE DRAWINGS

FIG. 8 is a diagram illustrating an example of a stored content in consumption information TI.

MODES FOR CARRYING OUT THE INVENTION

1. Embodiment

Figure 1:
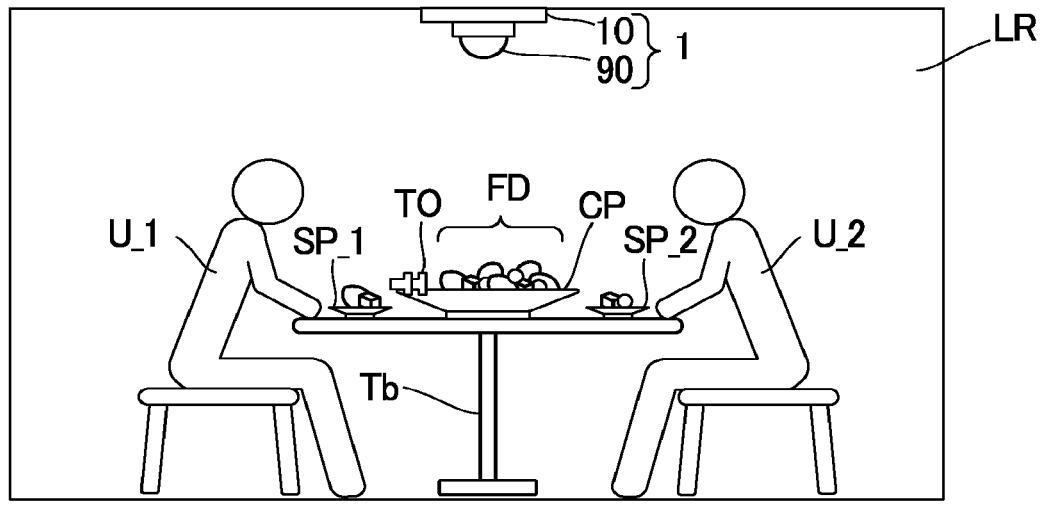
FIG. 1 is a diagram illustrating a summary of a dietary consumption estimating system 1.

The following is a description of a dietary consumption estimating system 1 according to an embodiment.
1.1 Summary of Dietary Consumption Estimating System 1
FIG. 1 is a diagram illustrating a summary of the dietary consumption estimating system 1. The dietary consumption estimating system 1 provides a service of estimating an amount of dietary consumption of a person U by photographically capturing the person U during a meal. The amount of the dietary consumption is the amount of food or beverage consumed by the person U. The "food or beverage" is one of "beverage" and "food." The amount of the food or beverage is, for example, the number of calories or grams of food if the "food or beverage" is food, or the number of calories or liters of beverage if the "food or beverage" is beverage. In the following, to facilitate description, a behavior in which "the person U consumes food or beverage" will be described simply as a behavior in which "the person U eats food", and the amount of the dietary consumption will be specifically described as the number of calories of the food eaten by the person U.

The dietary consumption estimating system 1 includes an information processing apparatus 10 and an image capturing apparatus 90. The information processing apparatus 10 is a computer used in the dietary consumption estimating system 1. In FIG. 1, the information processing apparatus 10 is attached to a ceiling of a room LR. The image capturing apparatus 90 is attached to the information processing apparatus 10.

In the room LR, multiple people U have a meal. In FIG. 1, as an example of the multiple people U, a person U_1 and a person U_2 have a meal in the room LR. The multiple people are not limited to two people, and may be three or more people. In the following description, reference numerals such as the person U_1 and the person U_2 are used to distinguish elements of the same type. In contrast, only the common signs in the reference numerals such as the person U are used when the elements of the same type are not distinguished from each other.

In the room LR, a dining table Tb is provided. On the dining table Tb, a platter CP, on which food FD to be eaten by the people U is served, and a plurality of small extra plates SP are arranged. The platter CP is an example of "a vessel of a first type to serve food or beverage to be consumed by multiple people." There may be one or more platters CP. The plurality of small extra plates SP is an example of "a plurality of vessels of a second type, on each of which a portion of the food or beverage is to be served." The dining table Tb is an example of "a table on which a vessel, which is to serve food or beverage to be consumed by multiple people, and a plurality of small extra plates, are arranged."

In FIG. 1, a small extra plate SP_1 for the person U_1 and a small extra plate SP_2 for the person U_2 are arranged on the dining table Tb, as an example of the plurality of small extra plates SP. The number of small extra plates SP is not limited to two, but may be three or more. Furthermore, on the platter CP, a pair of tongs TO is arranged which is used to move the food FD. In some regions, as illustrated in FIG. 1, it is customary for food FD to be served on a platter CP and then each person U takes food FD served on the platter CP onto a small extra plate SP to eat the food FD from the small extra plate SP. In addition, the person U may eat the food FD directly from the platter CP while eating the food FD served on the small extra plate SP. The small extra plate SP is a plate used to move a portion of the food FD for each person. Generally, the small extra plate SP is smaller than the platter CP.

The pair of tongs TO is an example of a "utensil for moving the food or beverage." In the following description, the utensil for moving the food or beverage is referred to as a "moving utensil." The moving utensils are divided broadly into a utensil for moving the food FD to portion out the food FD and a utensil for moving the food FD to eat the food FD directly. The utensil for moving the food FD to portion out the food FD is, for example, tongs TO, long chopsticks (long chopsticks for serving food), and spoons for serving food. The utensil for moving the food FD to eat the food FD directly from the platter CP is, for example, chopsticks, a spoon SO illustrated in FIG. 7, and a knife and fork.

Figure 2:
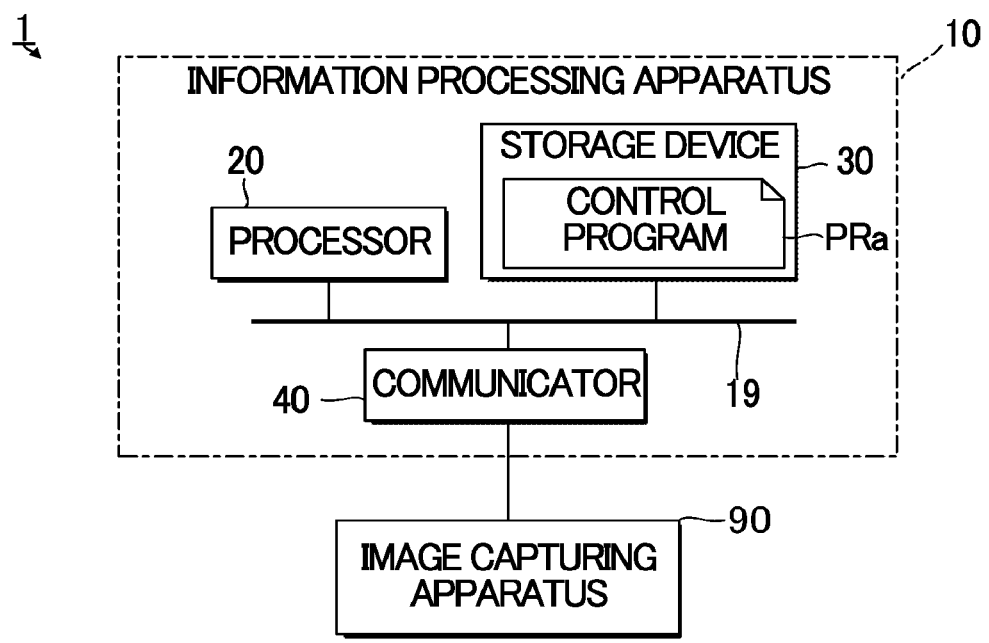
FIG. 2 is a block diagram illustrating a hardware configuration of the dietary consumption estimating system 1.

FIG. 2 is a block diagram illustrating a hardware configuration of the dietary consumption estimating system 1. The dietary consumption estimating system 1 includes the information processing apparatus 10 and the image capturing apparatus 90, as illustrated in FIG. 1.

Figure 3:
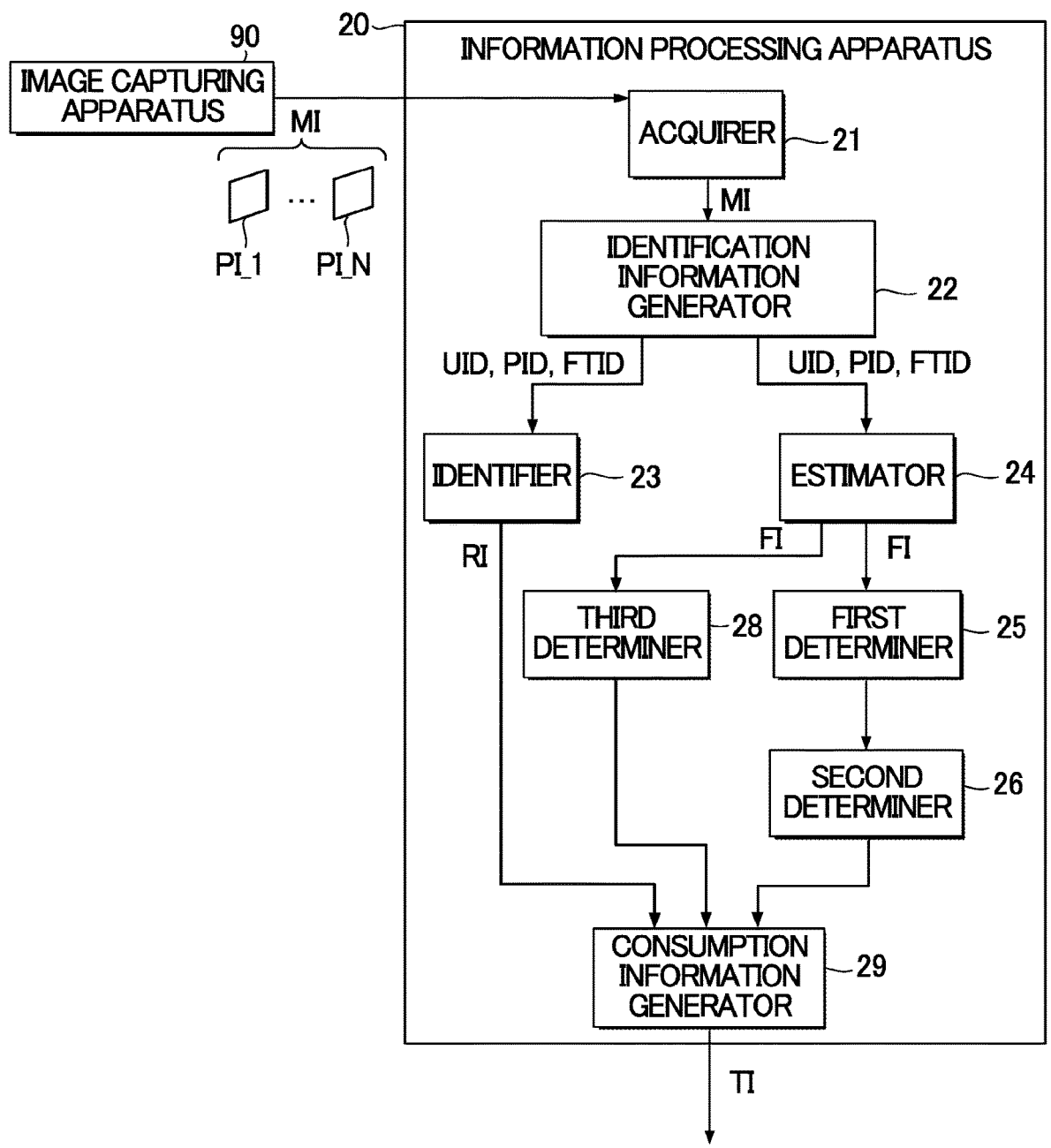
FIG. 3 is a block diagram illustrating functions of the dietary consumption estimating system 1.

The image capturing apparatus 90 generates video image information MI illustrated in FIG. 3 by photographically capturing the dining table Tb, on which the platter CP and the plurality of small extra plates SP are arranged, and the multiple people U. The video image information MI includes image information PI indicative of a still image P for each of a plurality of frames. The video image information MI includes pieces of image information PI_1 to PI_N. N is an integer of two or more. The image capturing apparatus 90 may photographically capture the entire body of person U, or may photographically capture the central torso of person U. The image capturing apparatus 90 includes, for example, an imaging optical system and an image sensor. The imaging optical system is an optical system including at least one photographic lens. The imaging optical system may include various optical elements such as a prism, or may include a zoom lens, a focusing lens, and the like. The image sensor may be, for example, a charge coupled device (CCD) image sensor or a complementary MOS (CMOS) image sensor, and the like.

The information processing apparatus 10 includes a processor 20, a storage device 30, a communicator 40, and a bus 19. The processor 20, the storage device 30, and the communicator 40 are accessed by each other through the bus 19 for communicating information. The bus 19 may be a single bus or may include different buses used for different devices.

The processor 20 is a processor that controls the entire information processing apparatus 10, and includes a central processing unit (CPU) including an interface, an arithmetic device, and registers. Note that some or all of the functions of the processor 20 may be implemented by hardware, such as by a digital signal processor (DSP), an application specific integrated circuit (ASIC), a programmable logic device (PLD), and a field programmable gate array (FPGA). The processor 20 executes various processes in parallel or sequentially.

The storage device 30 is a recording medium that is readable by the processor 20, and stores a plurality of programs including a control program PRa to be executed by the processor 20, and various information to be used by the processor 20. The storage device 30 includes, for example, one or more types of memory circuits, such as a read only memory (ROM), an erasable programmable ROM (EPROM), and an electrically erasable programmable ROM (EEPROM), and a random access memory (RAM).

The communicator 40 is a device that communicates with other devices, and the communicator 40 is referred to as a network device, a network controller, a network card, or a communication module, for example. The communicator 40 is capable of communicating with the image capturing apparatus 90.

1.2 Functions of Dietary Consumption Estimating System 1

FIG. 3 is a block diagram illustrating functions of the dietary consumption estimating system 1. The processor 20 reads the control program PRa from the storage device 30. The processor 20 functions as an acquirer 21, an identification information generator 22, an identifier 23, an estimator 24, a first determiner 25, a second determiner 26, a third determiner 28, and a consumption information generator 29 by executing the control program PRa.

The acquirer 21 acquires the video image information MI from the image capturing apparatus 90. The video image information MI indicates a video image obtained by the image capturing apparatus 90 photographically capturing the dining table Tb, on which the platter CP and the plurality of small extra plates SP are arranged, and the multiple people U.

The identification information generator 22 generates, based on the video image information MI, person identification information UID for identifying each of the multiple people U, plate identification information PID for identifying each of the platter CP and the plurality of small extra plates SP, and food identification information FTID for identifying the type of food. The person identification information UID is an example of "first identification information." The plate identification information PID is an example of "second identification information." The food identification information FTID is an example of "third identification information." The type of food is, for example, a noodle dish, a vegetable dish, a meat dish, a seafood dish, etc. For example, the identification information generator 22 extracts features included in the still image P for each of the plurality of frames included in the video image information MI to identify the person U, the plate, and the type of food FD. The identification information generator 22 assigns, based on identification results, unique identification information to the people U, the plates, and the type of food. The identification information generator 22 assigns the same identification information to each of the same person U, the same plate, and the same type of food that exist in different frames.

In this embodiment, to facilitate description, the reference numeral assigned to the person U is used as the person identification information UID. For example, the person identification information UID of the person U_1 is "U_1." Similarly, the reference numeral assigned to each of the platter CP and the small extra plates SP is used as the plate identification information PID. The food identification information FTID is, for example, FT_1 indicative of a noodle dish, and FT_2 indicative of a vegetable dish, etc.

A method of identifying the platter CP and the small extra plate SP is one of two methods described below, for example. In a first identifying method, the identification information generator 22 identifies a plate larger than a predetermined size as platter CP, and identifies a plate smaller than or equal to the predetermined size as small extra plate SP. Generally, the diameter of platter CP is 25 cm or more. The diameter of small extra plate SP is between 10 cm and 15 cm. Therefore, the predetermined size is, for example, a value greater than 15 cm and less than 25 cm as a diameter of a plate. In a second identifying method, in advance, part or all of the platter CP is colored a first color, and part or all of the small extra plate SP is colored a second color. When the color of the image of the plate included in the still image P is the first color, the identification information generator 22 identifies the plate of the first color as the platter CP. When the color of the image of the plate included in the still image P is the second color, the identification information generator 22 identifies the plate of the second color as the small extra plate SP.

The identifier 23 identifies, based on the video image information MI, which of the multiple people U each of the plurality of small extra plates SP corresponds to. For example, the identifier 23 identifies an association between the small extra plates SP and the people U in accordance with one of the following two identifying methods.

In a first identifying method, the identifier 23 calculates a distance between a small extra plate SP, which is a target to be associated with one of the multiple people U, among the plurality of small extra plates SP and each of the multiple people U. "The small extra plate SP, which is the target" is an example of "one vessel of the plurality of vessels" about the identifier 23. Then, the identifier 23 identifies a person U, who is positioned at the shortest distance among a plurality of calculated distances, as a person U corresponding to the small extra plate SP that is the target to be associated. The distance between the small extra plate SP and the person U is, for example, one of two modes described below. The distance in a first mode is a distance from an edge, which is closest to the person U among edges of the small extra plate SP, to an edge that is closest to the small extra plate SP among edges of the person U. The distance in a second mode is a distance from a center of gravity of the small extra plate SP to a center of gravity of the person U. The center of gravity is a point at which the sum of the cross-sectional primary moments of a target shape in plan view is zero, and is the intersection of the diagonal lines if it is a rectangular shape. In the following, the distance between the small extra plate SP and the person U will be described as the distance in the second mode.

Figures 4, 5:
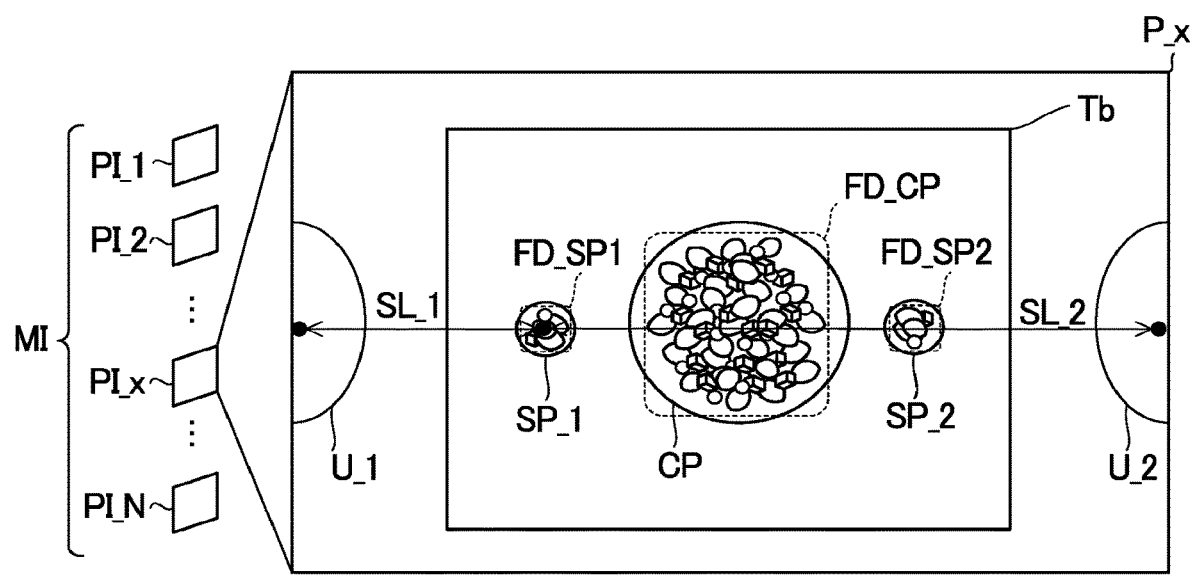
FIG. 4 is a diagram illustrating a first identifying method by an identifier 23.
FIG. 5 is a diagram illustrating an example of association information RI.

FIG. 4 is a diagram illustrating the first identifying method by the identifier 23. FIG. 4 illustrates a still image P_x indicated by a piece of image information PI_x included in the video image information MI. The sign "x" may be any integer from 1 to N. The still image P_x illustrated in FIG. 4 includes an image of the person U_1, an image of the person U_2, an image of the platter CP, an image of the small extra plate SP_1, an image of the small extra plate SP_2, an image of food FD_CP, an image of food FD_SP1, and an image of food FD_SP2. The food FD_CP is food served on the platter CP. The food FD_SP1 is food moved onto the small extra plate SP_1. The food FD_SP2 is food moved onto the small extra plate SP_2. The identifier 23 determines a distance SL between the small extra plate SP_1 and each of the multiple people U based on the still image P_x. For example, the identifier 23 calculates a distance SL_1 between the small extra plate SP_1 and the person U_1 and a distance SL_2 between the small extra plate SP_1 and the person U_2. FIG. 4 illustrates a black circle in the person U_1 indicative of the center of gravity of the person U_1, a black circle in the person U_2 indicative of the center of gravity of the person U_2, and a black circle in the small extra plate SP_1 indicative of the center of gravity of the small extra plate SP_1. As illustrated in FIG. 4, the identifier 23 identifies the person U_1, who is positioned at the shortest distance SL_1 among the distance SL_1 and the distance SL_2, as a person U corresponding to the small extra plate SP_1. Although not illustrated in FIG. 4, as for the small extra plate SP_2, the identifier 23 identifies the small extra plate SP_2 as the target to be associated, and identifies a person U corresponding to the small extra plate SP_2 in accordance with the same method as the method for the small extra plate SP_1.

In the first identification method, to enhance the accuracy of identifying the person U corresponding to the small extra plate SP, the identifier 23 preferably identifies the person U corresponding to the small extra plate SP for each of a plurality of still images P. The identifier 23 identifies a person U, who is most frequently identified as the person U corresponding to the small extra plate SP, as the person U corresponding to the small extra plate SP.

In the second identification method, the identifier 23 identifies, based on the video image information MI, a moving utensil overlapping the small extra plate SP. The identifier 23 identifies a person U, who has a hand holding the identified moving utensil, as the person U corresponding to the small extra plate SP. For example, the identifier 23 extracts a piece of image information PI indicative of a still image P, in which the small extra plate SP and the moving utensil overlap one over the other, from the video image information MI, and analyzes a still image P indicated by the extracted piece of image information PI to identify the person U having the hand holding the moving utensil.

To enhance the identification accuracy in the second identifying method, the identifier 23 preferably extracts a plurality of pieces of image information PI indicative of the still image P, in which the small extra plate SP and the moving utensil overlap one on the other, from the video image information MI, and preferably identifies, for each piece of image information PI, the person U corresponding to the small extra plate SP that is the target to be associated. The identifier 23 identifies a person U, who is most frequently identified as the person U corresponding to the small extra plate SP that is the target to be associated, as the person U corresponding to the small extra plate SP that is the target to be associated.

The identifier 23 outputs association information RI indicative of the association between the small extra plates SP and the people U.

FIG. 5 is a diagram illustrating an example of the association information RI. The association information RI indicates the association between the plate identification information PID indicative of the small extra plate SP and the person identification information UID indicative of the person U corresponding to the small extra plate SP. In FIG. 5, the association information RI indicates the small extra plate SP_1 associated with the person U_1, and the small extra plate SP_2 associated with the person U_2.

Although not illustrated in FIG. 5, multiple small extra plates SP may be associated with the same person U. This is because, to avoid mixing flavors of multiple foods FD, one person U may use multiple small extra plates SP that correspond to the multiple foods FD, respectively. For example, when a person U uses one small extra plate SP for meat dishes and another small extra plate SP for seafood dishes, the number of small extra plates SP corresponding to the person U is two. Furthermore, there may be a person U who is not associated with any of the small extra plates SP. Therefore, the number of persons U and the number of small extra plates SP may be the same or may be different from each other.

Description will now be given returning to FIG. 3. The estimator 24 estimates, based on the video image information MI, an amount of the food FD served on each of the platter CP and the plurality of small extra plates SP. For example, the storage device 30 stores the number of calories per unit area of food FD for each type of food FD. As an example of the stored content, the storage device 30 stores the number of calories per unit area of noodle dishes to be c1 calories. Similarly, the storage device 30 stores the number of calories per unit area of vegetable dishes to be c2 calories, and stores the number of calories per unit area of meat dishes to be c3 calories, and stores the number of calories per unit area of seafood dishes to be c4 calories. Values c1, c2, c3, and c4 are real numbers greater than zero. With regard to the still image P indicated by the image information PI included in the video image information MI, the estimator 24 measures an area of an image of the food FD included in the still image P to estimate a value, which is obtained by multiplying a value obtained by dividing the unit area into the measured area by the number of calories corresponding to the type of the food FD identified by the identification information generator 22, as the amount of the food FD.

The estimator 24 estimates the amount of the food FD served in each of the platter CP and the plurality of small extra plates SP based on a piece of image information PI indicative of a still image P, in which neither the platter CP nor the plurality of small extra plates SP are blocked by an object, among a plurality of pieces of image information PI in the video image information MI. The aforementioned object is, for example, a person U, a moving utensil, and a cup, etc. Neither the platter CP nor the plurality of small extra plates SP being blocked by the object may mean all of the platter CP and the plurality of small extra plates SP not being blocked by the object, or it may mean a part of the platter CP and a part of one small extra plate SP of the plurality of small extra plates SP not being blocked by the object. In the following explanation, neither the platter CP nor the plurality of small extra plates SP being blocked by the object means all of the platter CP and the plurality of small extra plates SP not being blocked by the object.

Figure 6:
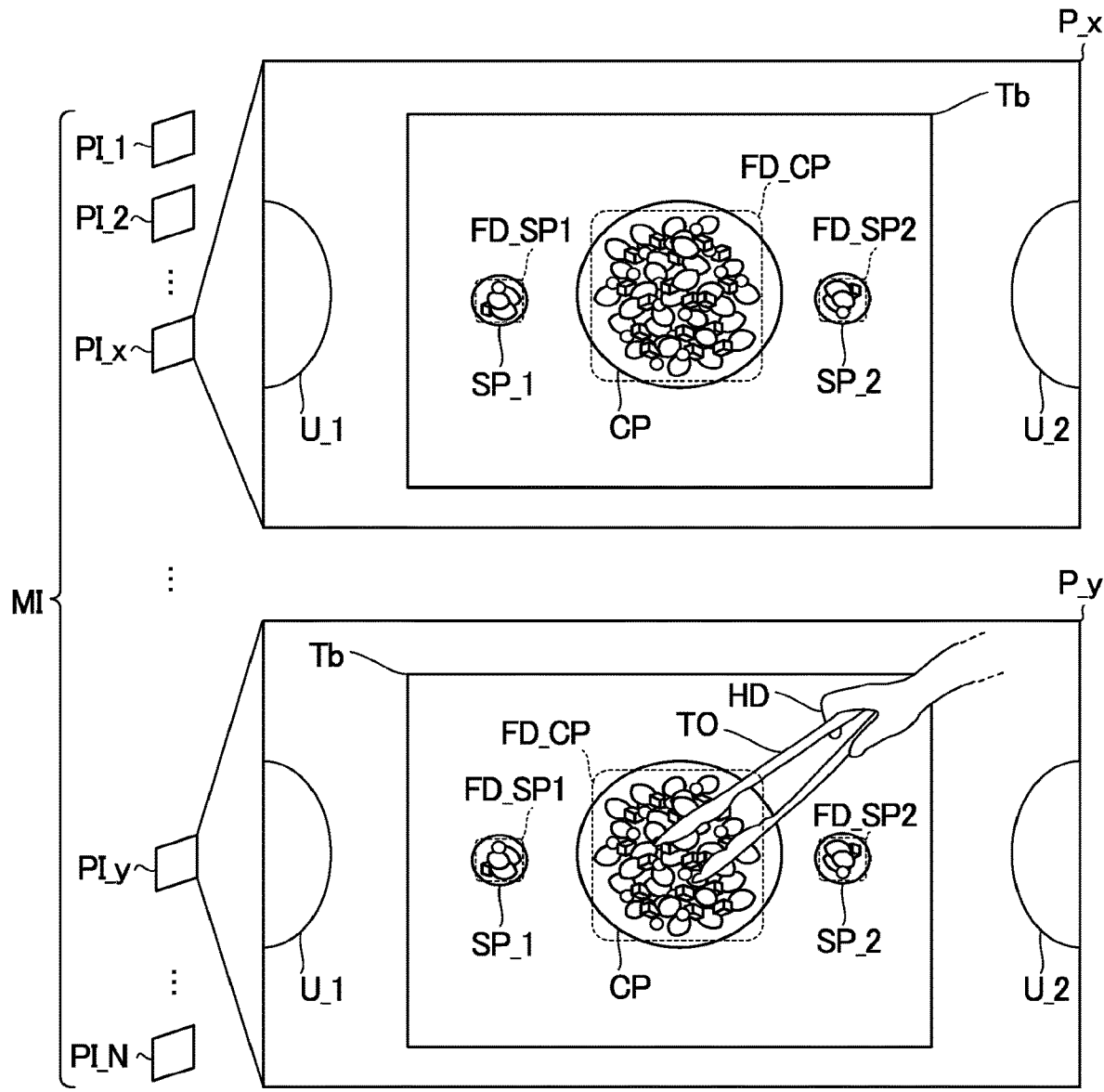
FIG. 6 is a diagram illustrating an example of a still image P in which neither a platter CP nor a plurality of small extra plates SP are blocked by an object.

FIG. 6 is a diagram illustrating an example of the still image P in which neither the platter CP nor the plurality of small extra plates SP are blocked by an object. FIG. 6 illustrates the still image P_x indicated by the piece of image information PI_x included in the video image information MI and a still image P_y indicated by a piece of image information PI_y. The still image P_x illustrated in FIG. 6 is identical to the still image P_x illustrated in FIG. 4. The still image P_y illustrated in FIG. 6 includes an image of the tongs TO and an image of a hand HD, in addition to the image of the person U_1, the image of the person U_2, the image of the platter CP, the image of the small extra plate SP_1, the image of the small extra plate SP_2, the image of the food FD_CP, the image of the food FD_SP1, and the image of the food FD_SP2. The hand HD is holding the tongs TO. To avoid complicating the drawing, in FIG. 6, the arm part corresponding to the hand HD is omitted The still image P_x represents no object blocking each of the platter CP and the plurality of small extra plates SP. On the other hand, in the still image P_y, a part of the platter CP is blocked by the tongs TO. Therefore, the estimator 24 estimates, based on the piece of image information PI_x indicative of the still image P_x, the amount of food FD served on each of the platter CP and the plurality of small extra plates.

The estimator 24 outputs food amount information FI indicative of the amount of the food FD served on each of the platter CP and the plurality of small extra plates SP. The food amount information FI indicates the number of calories of the food FD_CP served on the platter CP and the number of calories of the food FD_SP served on each of the plurality of small extra plates SP.

Description will now be given returning to FIG. 3. The first determiner 25 determines, based on the video image information MI, whether an amount of the food FD_CP served on the platter CP is decreased compared to an amount of the food FD_CP served on the platter CP at a point in time that is a predetermined period prior to a point in time of a determination. The predetermined period may be a freely selected period, but the predetermined period is preferable determined by considering the typical rate at which a person eats food. For example, the predetermined period may be a period of one minute or more but less than five minutes. The first determiner 25 determines that the amount of the food FD_CP served on the platter CP is decreased when a value, which is obtained by subtracting an amount of the food FD_CP served on the platter CP at the current point in time (the point in time of the determination) from the amount of the food FD_CP served on the platter CP at the point in time that is the predetermined period prior to the point in time of the determination, is greater than or equal to a predetermined threshold.

When a result of a determination by the first determiner 25 is affirmative, the second determiner 26 determines, based on the video image information MI, whether the food FD_CP on the platter CP was directly eaten by one person U of the multiple people U, or the food FD_CP was moved from the platter CP onto one small extra plate SP of the plurality of small extra plates SP. The one person U is an example of "one person of the multiple people." For example, the second determiner 26 uses one of two determining methods described below.

In a first determining method, the second determiner 26 determines whether an amount of the food FD_SPi served on each small extra plate SP_i of the plurality of small extra plates SP is increased compared to an amount of the food FD_SP served on each small extra plate SP_i at a point in time that is the predetermined period prior to a point in time of a determination. Sign "i" is each integer from 1 to the total number of small extra plates SP. When a small extra plate SP_i is present on which the food FD_SP is increased, the second determiner 26 determines that the food FD_CP was moved onto the one small extra plate SP. On the other hand, when no small extra plate SP_i is present on which the food FD_SP is increased, it means that the one person U ate the food FD_CP directly from the platter CP. Therefore, the second determiner 26 determines that a person U ate the food FD_CP from the platter CP.

In a second determining method, when the result of the determination by the first determiner 25 is affirmative, the second determiner 26 starts to track a destination of the food FD_CP served on the platter CP based on the video image information MI. Then, the second determiner 26 identifies, based on the video image information MI, a person U having a hand holding a moving utensil moving the food FD_CH being tracked. Then, the second determiner 26 determines, based on the video image information MI, whether the food FD_CH being tracked disappears without being moved onto the plurality of small extra plates SP. When the food FD_CP disappears, the person U having the hand holding the moving utensil is the person U who ate the food FD directly from the platter CP, and therefore, the second determiner 26 determines that the person U having the hand holding the moving utensil is the person U who ate the food FD_CH served on the platter CP. On the other hand, when the food FD_CH being tracked is moved onto one small extra plate SP among the plurality of small extra plates SP, the second determiner 26 determines that the food FD_CH was moved onto the one small extra plate SP.

Figure 7:
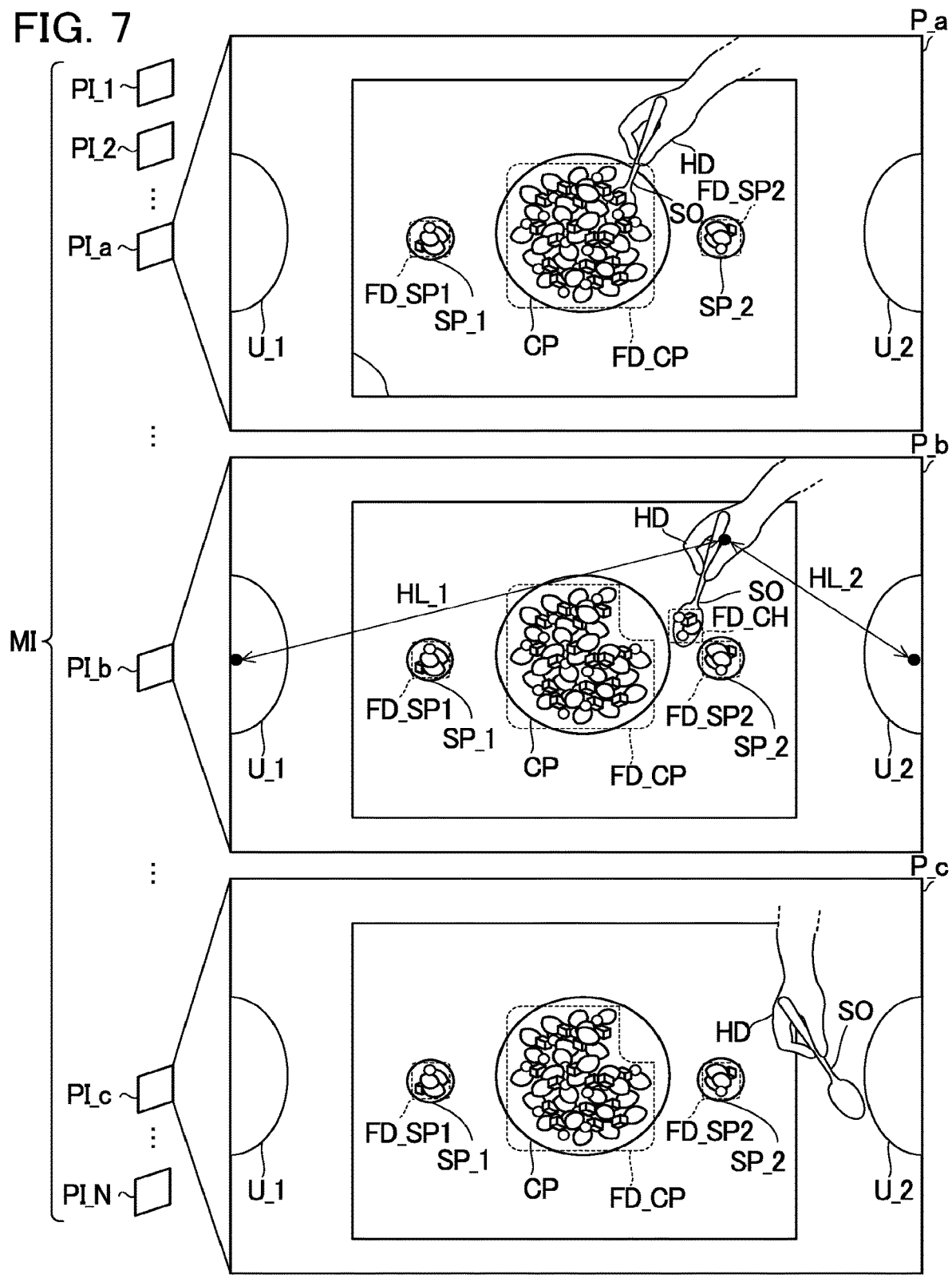
FIG. 7 is a diagram illustrating a second determining method by a second determiner 26.
Figure 9:
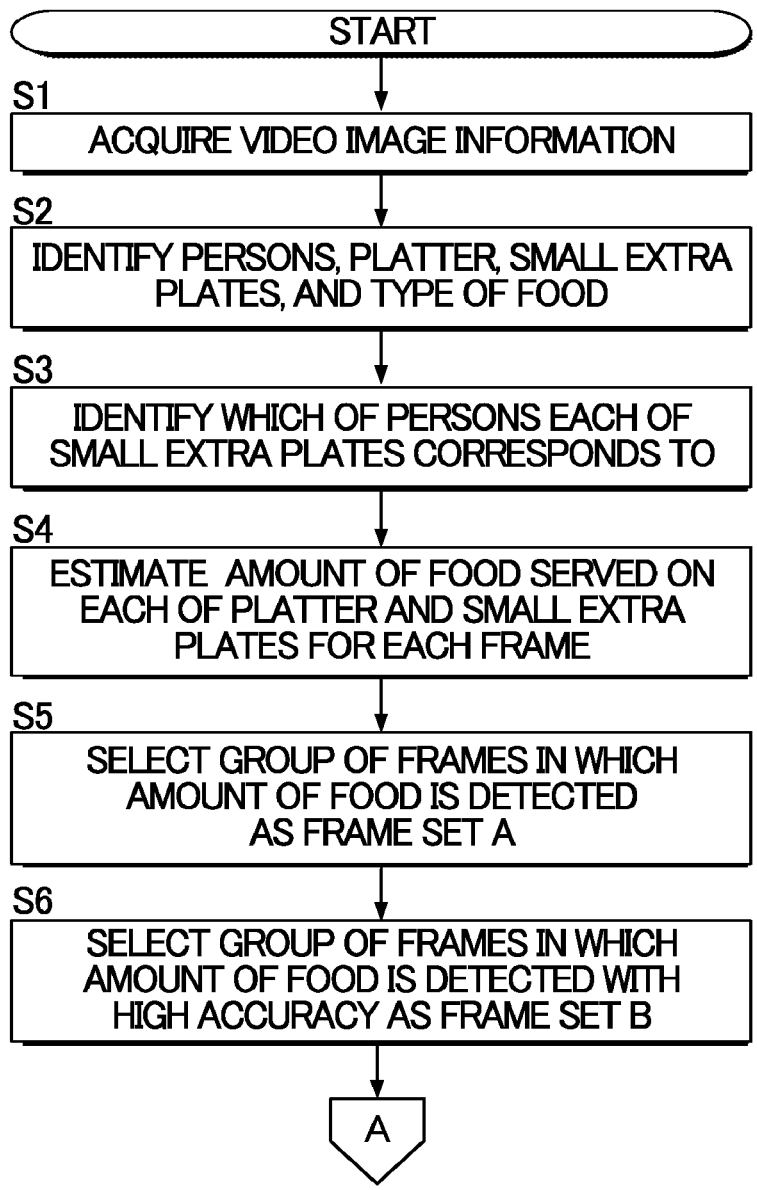
FIG. 9 is a flowchart illustrating an operation of the dietary consumption estimating system 1 (Part 1).

FIG. 7 is a diagram illustrating the second determining method by the second determiner 26. FIG. 7 illustrates a still image P_a indicated by a piece of image information PI_a included in the video image information MI, a still image P_b indicated by a piece of image information PI_b, and a still image P_c indicated by a piece of image information PI_c. Values a, b, and c are integers ranging from 1 to N, and have a relationship a<b<c.

The still image P_a, the still image P_b, and the still image P_c include an image of the spoon SO and the image of the hand HD, in addition to the image of the person U_1, the image of the person U_2, the image of the platter CP, the image of the small extra plate SP_1, the image of the small extra plate SP_2, the image of the food FD_CP, the image of the food FD_SP1, and the image of the food FD_SP2.

Based on the still image P_b, the first determiner 25 determines that the amount of the food FD_CP served on the platter CP is decreased compared to the amount of the food FD_CP served on the platter CP at a point in time at which the still image P_a was captured. Therefore, the second determiner 26 starts to track the destination of the food FD_CP served on the platter CP based on the still image P_b. From a point in time at which the still image P_b is obtained, the second determiner 26 starts to track the food FD_CH served on the spoon SO. The food FD_CH to be tracked is food being a part of the food FD_CP served on the platter CP at a point in time at which the still image P_a was captured. The second determiner 26 identifies the person U having the hand holding the spoon SO moving the food FD_CH to be tracked.

The method of identifying the person U having the hand holding the moving utensil is one of two modes described below. In an identifying method in a first mode, the second determiner 26 extracts the contour of the arm connected to the hand holding the moving utensil to identify the person U connected to the extracted contour of the arm as the person U having the hand holding the moving utensil.

In an identifying method in a second mode, the second determiner 26 calculates a distance between the hand holding the moving utensil and each of the multiple people U to identify the person U who is positioned at the shortest distance among the plurality of calculated distances, as the person U having the hand holding the moving utensil. The distance between the hand holding the moving utensil and the person U is, for example, one of two modes described below. The distance in a first mode is a distance from an edge, which is closest to the person U among edges of the hand holding the moving utensil, to an edge that is closest to the hand holding the moving utensil among edges of the person U. The distance in a second mode is a distance from a center of gravity of the hand holding the moving utensil to a center of gravity of the person U. In the following, the distance between the hand holding the moving utensil and the person U will be described as the distance in the second mode.

In an example of the still image P_b, the second determiner 26 calculates each of a distance HL_1 between the hand HD holding the spoon SO and the person U_1, and a distance HL_2 between the hand HD and the person U_2. The still image P_b illustrates a black circle in the person U_1 indicative of the center of gravity of the person U_1, a black circle in the person U_2 indicative of the center of gravity of the person U_2, and a black circle in the hand HD indicative of the center of gravity of the hand HD. As shown in the still image P_b, the second determiner 26 determines the person U_2, which is positioned at the shortest distance HL_2 among the distance HL_1 and the distance HL_2, as the person U having the hand holding the spoon SO.

In the still image P_c, the food FD_CH to be tracked disappears without being moved onto the plurality of small extra plates SP. Therefore, the second determiner 26 determines that the person U_2, who is identified as the person U having the hand holding the spoon SO, ate the food FD served on the platter CP.

Description will now be given returning to FIG. 3. The third determiner 28 determines whether an amount of the food FD_SP served on one small extra plate SP among the plurality of small extra plates SP is decreased compared to an amount of the food FD_SP served on the one small extra plate SP at a point in time that is the predetermined period prior to a point in time of a determination.

The consumption information generator 29 generates consumption information TI based on a result of a determination by the second determiner 26, a result of a determination by the third determiner 28, and the association information RI output by the identifier 23. A trigger to generate the consumption information TI is one of two triggers described below.

A first trigger is the result of the determination by the second determiner 26 indicating that the one person U ate the food FD_CP served on the platter CP. In this case, the consumption information generator 29 generates the consumption information TI in which an amount of food FD eaten by this person U, this person U, and the type of food FD eaten by this person U are associated with each other. In more detail, the consumption information TI is information in which the amount of the food FD, the person identification information UID identifying the person U who ate the food FD, and the FTID identifying the type of the food FD are associated with each other. When the result of the determination by the second determiner 26 indicates that the food was moved onto one small extra plate SP, the estimator 24 increases the amount of the food FD_SP served on this small extra plate SP, by the decrease in amount of food FD_CP served on the platter CP.

A second trigger is the result of a determination by the third determiner 28 being affirmative, that is, a decrease in an amount of the food FD_SP served on one small extra plate SP. In this case, the consumption information generator 29 generates the consumption information TI in which the person U associated with this small extra plate SP, the amount of the food FD decreased from the food FD_SP served on this small extra plate SP, and the type of this food FD are associated with each other.

FIG. 8 is a diagram illustrating an example of a stored content in the consumption information TI. FIG. 8 illustrates pieces of consumption information TI_1 through consumption information TI_M. M is an integer greater than or equal to 1. The consumption information TI illustrated in FIG. 8 is information in which time information and consumption mode information in addition to the person identification information UID, the amount of the food FD, and the food identification information FTID are associated with each other. The time information and the consumption mode information may not be included in the consumption information TI. The time information indicates time at which the person U ate the food FD. The consumption mode information indicates whether the person U ate the food FD directly from the platter CP or the person U ate the food FD from the small extra plate SP.

The consumption information generator 29 generates the piece of consumption information TI_1 and the piece of consumption information TI_2 in response to the second trigger described above, and generates the piece of consumption information TI_M in response to the first trigger. The piece of consumption information TI_1 indicates that the person U_1 ate the food of the type corresponding to FT_1 for xx calories from the small extra plate SP_1 at 12:00:01.

The consumption information generator 29 outputs the generated consumption information TI to the storage device 30 or the communicator 40.

1.3 Operation of Dietary Consumption Estimating System 1

The operation of the dietary consumption estimating system 1 will be described with reference to FIGS. 9 to 11b.

FIG. 9, FIG. 10, FIG. 11A, and FIG. 11B are each a flowchart illustrating the operation of the dietary consumption estimating system 1. A trigger to start the operation illustrated by FIG. 9, FIG. 10, FIG. 11A, and FIG. 11B is, for example, one of two triggers described below. A first trigger is completion of generation of the video image information MI, which indicates a video image including an image of the person U during a meal, by the image capturing apparatus 90 in response to an end of the meal by the person U. A second trigger is generation of the video image information MI, which includes a predetermined number of still images P, by the image capturing apparatus 90.

The processor 20, by functioning as the acquirer 21, acquires the video image information MI from the image capturing apparatus 90 (step S1). Then, the processor 20, by functioning as the identification information generator 22, identifies the multiple people U, the platter CP, the plurality of small extra plates SP, and the type of food FD served on the platter CP or the small extra plate SP (step S2).

Then, the processor 20, by functioning as the identifier 23, identifies which of the multiple people U each of the plurality of small extra plates SP corresponds to (step S3). Then, the processor 20, by functioning as the estimator 24, estimates, based on the extracted frame, the amount of the food served on each of the platter CP and the plurality of small extra plates SP (step S4). The processor 20, by functioning as the estimator 24, selects a group of frames, in which the amount of the food FD is detected, from the video image information MI as a frame set A (step S5). Furthermore, the processor 20, by functioning as the estimator 24, selects a group of frames in which the amount of the food is detected with high accuracy as a frame set B (step S6). The group of frames in which the amount of the food is detected with high accuracy is, in other words, a group of frames in which the platter CP and the plurality of small extra plates SP are not blocked by an object.

Figure 10:
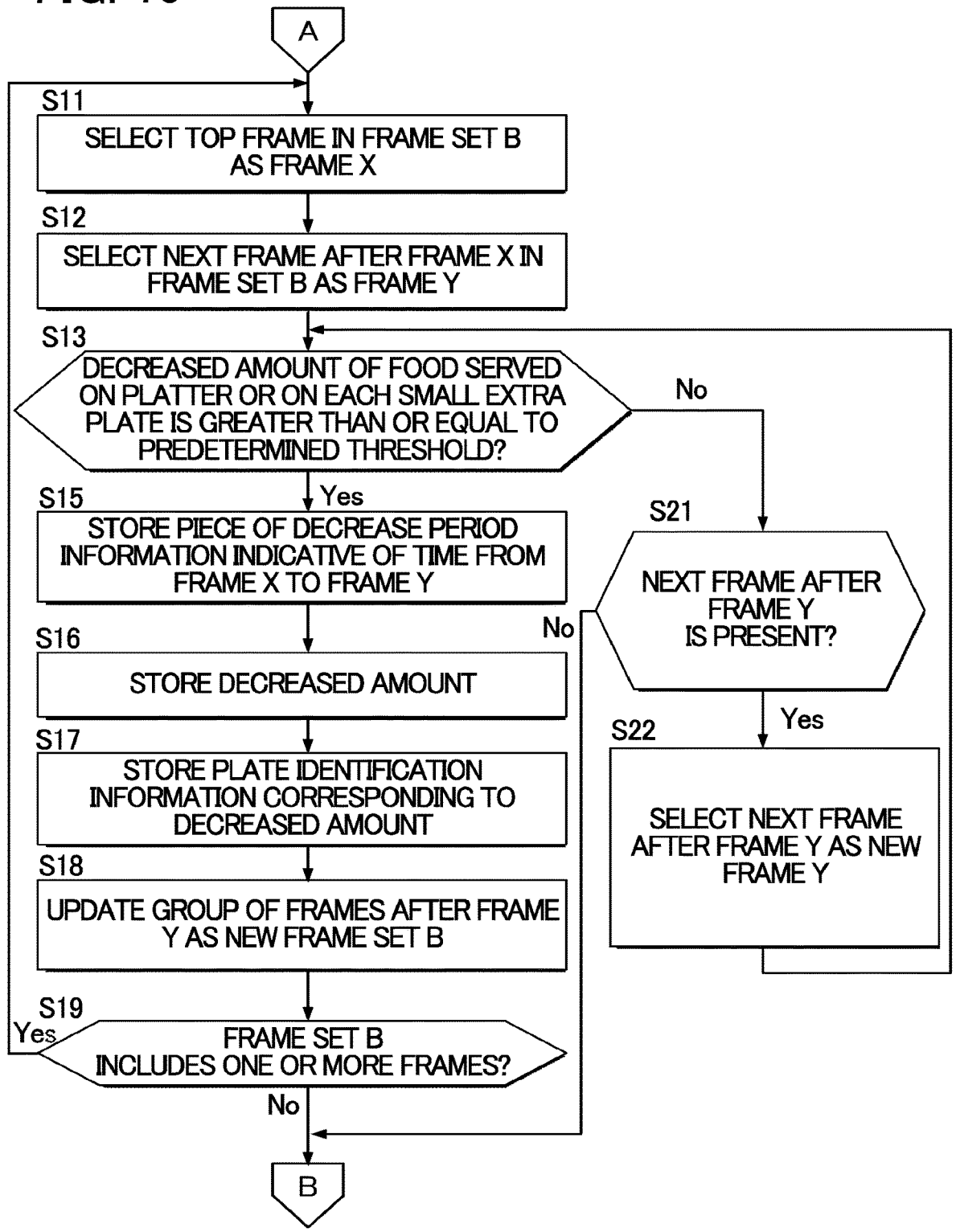
FIG. 10 is a flowchart illustrating the operation of the dietary consumption estimating system 1 (Part 2).

In FIG. 10, the processor 20 selects a top frame in the frame set B as a frame X (step S11). Then, the processor 20 selects a next frame after the frame X in the frame set B as a frame Y (step S12). Then, the processor 20, by functioning as the first determiner 25 or the third determiner 28, determine whether a decreased amount ΔFD of the food FD served on the platter CP or on each of the plurality of small extra plates SP in the frame Y compared to the frame X is greater than or equal to the predetermined threshold (step S13). In other words, in the processing of step S13, the processor 20 determines whether one of a decreased amount ΔFD_CP and a decreased amount ΔFD_SPi that are described below is greater than or equal to the predetermined threshold. Each variable i is an integer from 1 to the total number of small extra plates SP.

ΔFD_CP=food FD_CP served on the platter CP in the frame X—food FD_CP served on the platter CP in the frame Y. ΔFD_SPi=food FD_SPi served on the small extra plate SP_i in the frame X—food FD_SPi served on the small extra plate SP_i in the frame Y.

When a result of a determination in step S13 is affirmative, the processor 20 stores a piece of information indicative of a time from the frame X to the frame Y in the storage device 30 as a piece of decrease period information (step S15). Then, the processor 20 stores the decreased amount ΔFD greater than or equal to the predetermined threshold in the storage device 30 (step S16). The processor 20 stores the plate identification information PID of the plate corresponding to the decreased amount ΔFD greater than or equal to the predetermined threshold in the storage device 30 (step S17). The storage device 30 stores the piece of decrease period information, the decreased amount ΔFD, and the plate identification information PID that are associated with each other.

Then, the processor 20 updates a group of frames after the frame Y in the frame set B as a new frame set B (step S18). When a position of the frame Y in the frame set B is at the end, the number of frames contained in the updated frame set B is 0.

The processor 20 determines whether the updated frame set B includes one or more frames (step S19). If a result of a determination in step S19 is affirmative, the processor 20 returns the processing to step S11.

Figure 11A:
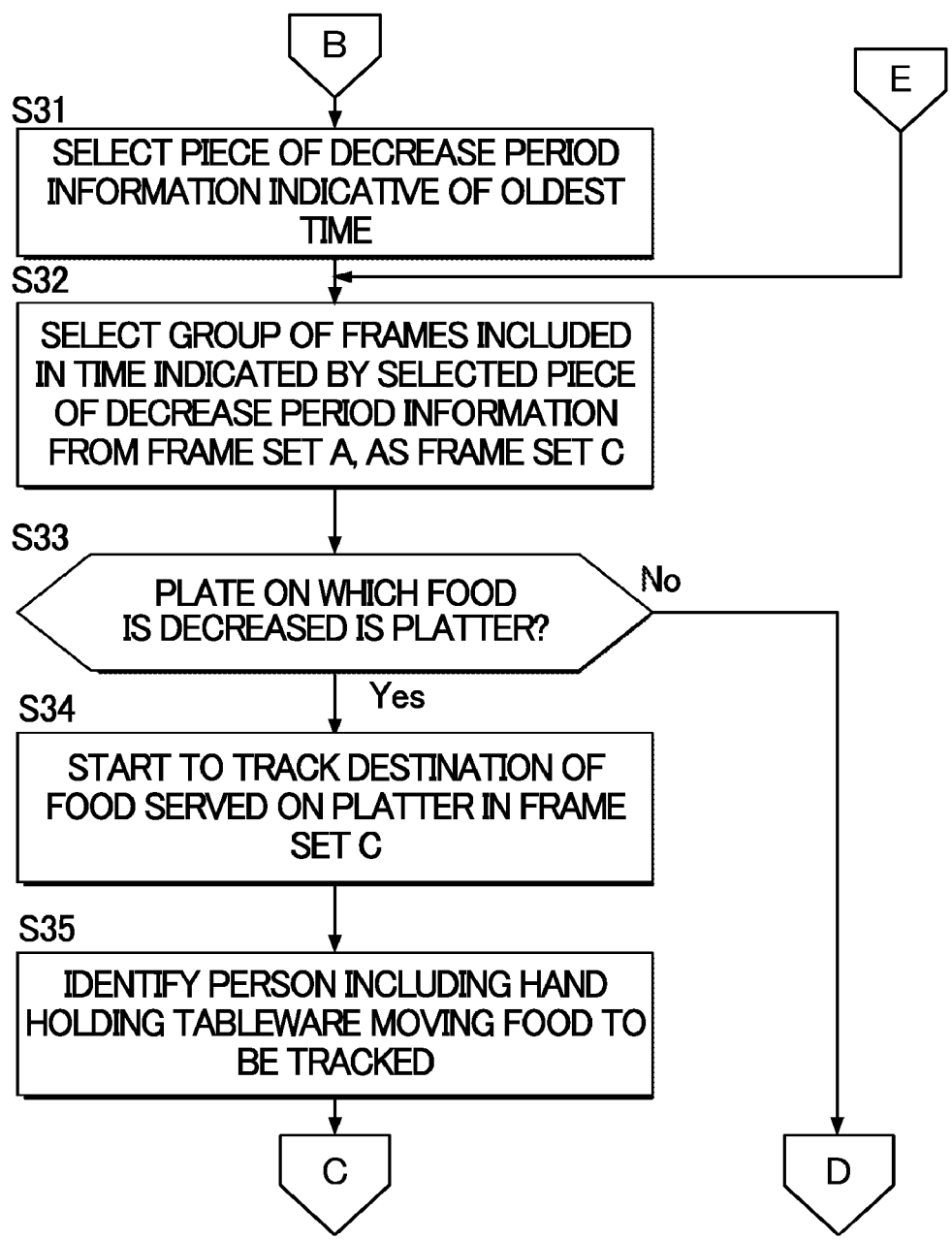
FIG. 11A is a flowchart illustrating the operation of the dietary consumption estimating system 1 (Part 3).
Figure 11B:
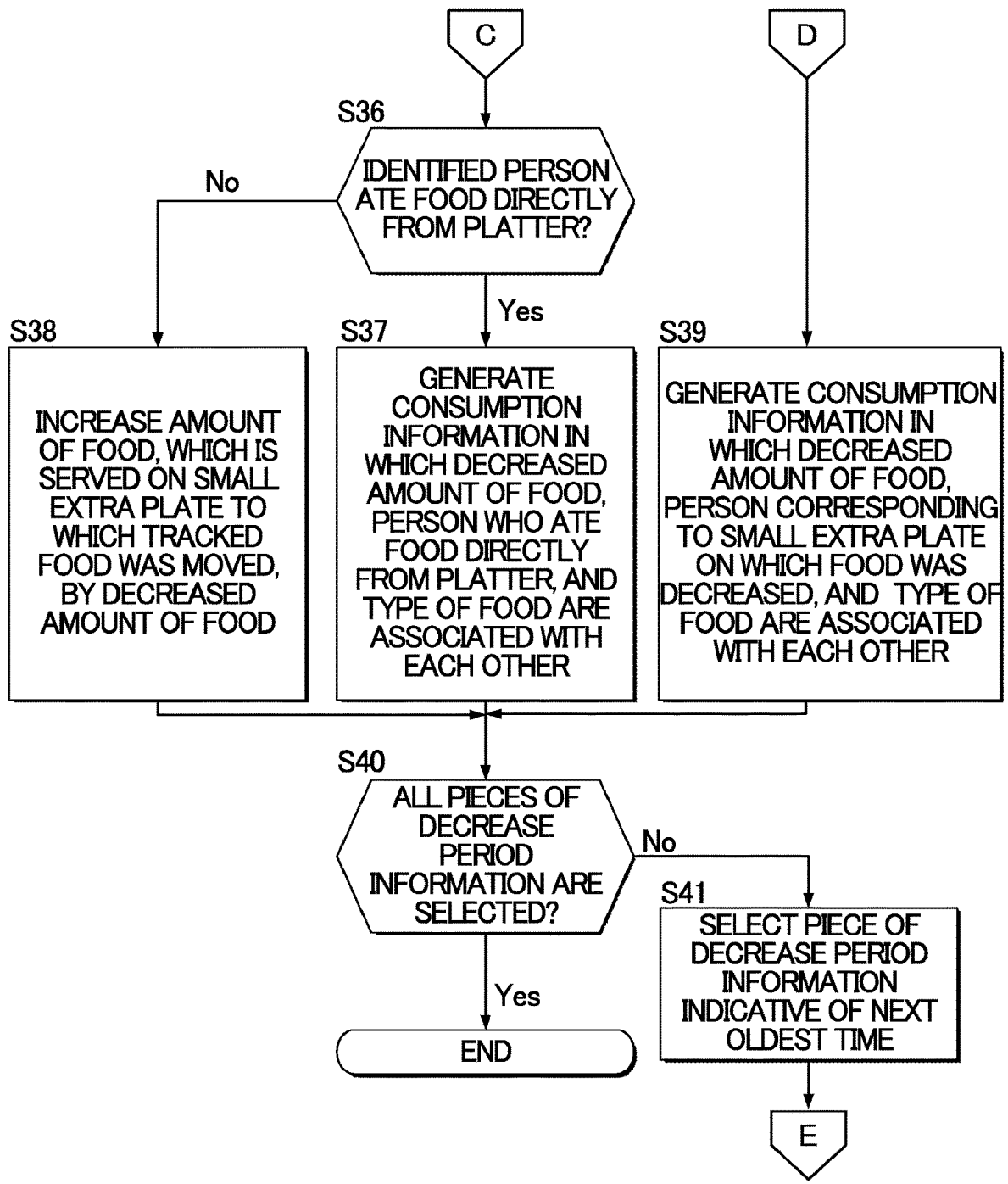
FIG. 11B is a flowchart illustrating the operation of the dietary consumption estimating system 1 (Part 4).

When the result of the determination in step S19 is negative, in other words, when the frame set B does not include any frames, in FIG. 11A, the processor 20 selects a piece of decrease period information indicative of the oldest time from among one or more pieces of decrease period information stored in the storage device 30 in the processing in step S15 (step S31).

If the result of the determination in step S13 is negative, in other words, when the decreased amount ΔFD_CP and the decreased amount ΔFD_SPi are all less than the predetermined threshold, the processor 20 determines whether a next frame after the frame Y in the frame set B is present (step S21). When a result of a determination in step S21 is affirmative, the processor 20 selects the next frame after the frame Y in the frame set B as a frame Y (step S22), and then executes the processing in step S13 again. On the other hand, when the result of the determination in step S21 is negative, the processor 20 executes the processing in step S31.

After completing the processing in step S31, the processor 20 selects a group of frames, which is included in the time indicated by the selected piece of decrease period information, from the frame set A as a frame set C (step S32).

The processor 20 refers to the plate identification information PID stored by the processing in step S17 to determine whether the plate on which the food FD is decreased is the platter CP or the small extra plate SP. Specifically, the processor 20 determines whether the plate on which the food FD is decreased is the platter CP (step S33). When a result of the determination is affirmative, in other words, when the plate on which the food FD is decreased is the platter CP (step S33: Yes), the processor 20, by functioning as the second determiner 26, starts to track the destination of the food FD_CP served on the platter CP in the frame set C (step S34). Then, the processor 20, by functioning as the second determiner 26, identifies the person U having the hand holding a piece of tableware moving the food FD_CH to be tracked (step S35). The processor 20, by functioning as the second determiner 26, determines whether the identified person U ate the food FD directly from the platter CP or the food FD was moved onto the small extra plate SP, based on the destination of the food FD_CH to be tracked. Specifically, the processor 20 determines whether the identified person U ate the food FD directly from the platter CP (step S36).

In step S33, the processor 20 may determine whether the plate on which the food FD is decreased is the small extra plate SP instead of determining whether the plate on which the food FD is decreased is the platter CP. Similarly, in step S36, the processor 20 may determine whether the food FD was moved onto the small extra plate SP instead of determining whether the identified person U ate the food FD directly from the platter CP.

When the identified person U ate the food FD directly from the platter CP, in other words, when the food FD_CH to be tracked disappears without being moved onto the plurality of small extra plates SP (step S36: Yes), the processor 20, by functioning as the consumption information generator 29, generates the consumption information TI in which the decreased amount ΔFD of the food FD, the person U who ate the food directly from the platter CP, and the type of food FD are associated with each other (step S37). On the other hand, when a result of a determination in step S36 is negative, in other words, when the food FD_CH to be tracked was moved onto the small extra plate SP (step S36: No), the processor 20, by functioning as the estimator 24, increases the amount of the food FD, which is served on the small extra plate SP onto which the food FD_CH to be tracked was moved, by the decreased amount ΔFD of the food FD (step S38).

When the result of the determination in step S33 is negative, in other words, when the plate on which the food FD is decreased is the small extra plate SP (step S33: No), the processor 20, by functioning as the consumption information generator 29, generates the consumption information TI in which the decreased amount ΔFD of the food FD, the person U corresponding to the small extra plate SP on which the food FD is decreased, and the type of the food FD are associated with each other (step S39).

After completing the processing in step S37, after completing the processing in step S38, or after completing the processing in step S39, the processor 20 determines whether all pieces of decrease period information are selected (step S40). When a result of a determination in step S40 is negative, in other words, when there is a piece of decrease period information not selected yet, the processor 20 selects a piece of the decrease period information that indicates the next oldest time after the time indicated by the currently selected piece of decrease period information (step S41), and then executes the processing in step S32. On the other hand, when the result of the determination in step S40 is affirmative, in other words, all the pieces of decrease period information are selected, the processor 20 ends a series of processing operations shown in FIG. 9, FIG. 10, FIG. 11A, and FIG. 11B.

According to the above description, when the amount of the food FD_CP served on the platter CP is decreased, the processor 20 determines whether one person U ate the food FD on the platter CP or the food FD was moved onto one small extra plate SP of the plurality of small extra plates SP. When the one person U ate the food FD from the platter CP, the processor 20 generates the consumption information TI in which the amount of the food FD eaten directly from the platter CP, the person U who ate the food directly from the platter CP, and the type of food FD are associated with each other. As described above, since the processor 20 generates the consumption information TI indicating that the person U ate the food FD directly from the platter CP, it is possible to accurately identify the amount of dietary consumption of the person U even if a person U exists who ate food directly from the platter CP.

Furthermore, when the amount of the food FD served on one small extra plate SP among the plurality of small extra plates SP is decreased, the processor 20 generates the consumption information TI in which the decreased amount of the food FD, the person U corresponding to the small extra plate SP on which the food FD is decreased, and the type of food FD are associated with each other. As described above, since the processor 20 generates the consumption information TI indicating that the person U ate the food from the small extra plate SP, it is possible to accurately determine the amount of dietary consumption of the person U, even if the food was moved onto the small extra plate SP.

The first identifying method by the identifier 23 includes calculating the distance between the small extra plate SP, which is a target to be associated, among the plurality of small extra plates SP and each of the multiple people U, and identifying the person U positioned at the shortest distance among the plurality of calculated distances as the person U corresponding to the small extra plates SP that is a target to be identified. According to the first identifying method, it is not necessary to find the still image P in which the small extra plate SP and the moving utensil overlap one over the other, compared to the second identifying method. Therefore, according to the first identifying method, it is possible to easily identify the person U corresponding to the small extra plate SP compared to the second identifying method.

Furthermore, the estimator 24 estimates the amount of the food FD served on each of the platter CP and the plurality of small extra plates SP based on the piece of image information PI, which indicates the still image P in which none of the platter CP and the plurality of small extra plates SP is blocked by an object, among the plurality of pieces of image information PI in the video image information MI. Estimating the amount of the food FD using a still image P, in which the platter CP or the plurality of small extra plates SP are blocked by an object, causes an error in which an estimated amount of the food is less than the actual amount when the food FD is hidden by the object. Therefore, by using the image information PI indicating that the still image P in which neither the platter CP nor the plurality of small extra plates SP are blocked by an object, the estimator 24 can improve the accuracy of the estimation of the amount of the food FD.

Furthermore, when the amount of the food FD_CP served on the platter CP is decreased, the second determiner 26 starts to track, based on the video image information MI, the destination of the food FD served on the platter CP. Then, the second determiner 26 identifies the person U having the hand holding the moving utensil carrying the moving food FD_CH, and determines that the person U having the hand holding the moving utensil ate the food FD_CP served on the platter CP when the moving food FD_CH disappears without being moved onto the plurality of small extra plates SP. Since it is confirmed that the moving food FD_CH disappears without being moved onto the plurality of small extra plates SP, it is accurately determined that the food FD was eaten directly from the platter CP.

Furthermore, as a method of identifying the person U having the hand holding the moving utensil in the second mode, the second determiner 26 calculates the distance between the hand holding the platter CP and each of the multiple people U based on the video image information MI, and identifies the person U positioned at the shortest distance among the calculated distances as the person U having the hand holding the platter CP. Compared to the identifying method in the first mode, the identifying method in the second mode does not require extraction of the contour of the arm of the hand holding the moving utensil. Therefore, the identifying method in the second mode can easily identify the person U having the hand holding the moving utensil, compared to the identifying method in the first mode.

2. Modifications

Each of the above modes can be modified in various ways. Specific modifications will be described below. Two or more modifications freely selected from the following modifications may be combined as long as no conflict arises from such a combination. It should be noted that, in the modifications illustrated below, elements having the same effects or functions as those in the embodiment are given the aforementioned reference numerals, and detailed description thereof will be omitted as appropriate.

(1) In the embodiment, it is described that the platter CP is an example of a vessel of the first type to serve food or beverage to be consumed by the multiple people; however, the vessel of the first type is not limited to a plate. For example, the vessel of the first type may be a pot, a cooked-rice container, etc. The cooked-rice container is a container into which cooked rice is transferred from a pot.

(2) In each mode described above, it is described that the plurality of small extra plates SP is an example of the plurality of vessels of the second type on each of which the part of the food or beverage is to be served; however, the vessels of the second type are not limited to plates. For example, the vessels of the second type may be tonsui bowls used to portion out food in a pot, or rice bowls used to portion out rice in a pot. The tonsui bowls are bowls with a protruding tongue at the rim.

(3) In each mode described above, it is described that the small extra plate SP is generally smaller than the platter CP; however, it is not limited to this. For example, some people U may move the food served on each of a plurality of platters CP onto one small extra plate SP. In this case, since a plurality of types of food FD is served on the small extra plate SP, the small extra plate SP may be almost as large as the platter CP, or the small extra plate SP may be larger than the platter CP.

When the platter CP and the small extra plate SP cannot be distinguished from each other by size in a situation in which the small extra plate SP is almost as large as the platter CP, the identification information generator 22 may identify the platter CP and the small extra plate SP by using, for example, a third identifying method described below or a fourth identifying method described below, as a method different from the second method of identifying the platter CP and the small extra plate SP described above. In the third identifying method, the identification information generator 22 identifies a plate on which the food FD is served at a point in time at which the meal is started, as the platter CP, and identifies a plate on which the food FD is not served at the point in time at which the meal is started, as the small extra plate SP. In the fourth identifying method, the identification information generator 22 identifies the platter CP and the small extra plate SP by a person U pointing to the platter CP and the small extra plate SP. The fourth identifying method will be described in more detail. As an assumption, the dietary consumption estimating system 1 includes an audio speaker. The identification information generator 22 causes the speaker to output an audio message to the effect that "Please point to a platter" for a predetermined number of seconds. The identification information generator 22 analyzes the video image information, which indicates the video image captured by the image capturing apparatus 90 after the aforementioned audio message, to identify the plate pointed to by the person U for the predetermined number of seconds as the platter CP. Similarly, the identification information generator 22 causes the speaker to output an audio message to the effect that "Please point to a small extra plate for a predetermined number of seconds, and after the predetermined number of seconds has elapsed, please point to another small extra plate that had not been pointed to for the predetermined number of seconds." The identification information generator 22 analyzes the video image information, which indicates the video image captured by the image capturing apparatus 90 after the aforementioned audio message, to identify the plate pointed to by the person U for the predetermined number of seconds as the small extra plate SP.

(4) In each mode described above, the food FD is moved from the platter CP onto the small extra plate SP and is eaten by the person U. Thus, in each of the modes described above, the food FD is eaten by the person U by using at most two plates, but it is not limited to this. For example, the food FD may be eaten by the person U by using three or more plates.

(5) In each mode described above, only a case is described in which the amount of the food FD served on the small extra plate SP is decreased by a person U eating the food; however, the food FD may be returned from the small extra plate SP to the platter CP, or the food FD may be moved onto another small extra plate SP. The processor 20, by tracking the destination of the food FD in response to a decrease in the amount of the food FD served on the small extra plate SP, can determine whether the food FD was eaten by the person U, the food FD was returned to the platter CP, or the food FD was moved onto another small extra plate.

(6) In each mode described above, food is used as the food or beverage to be moved, but beverages may also be used. For example, each of the modes described above may be applied to a case in which soup in a deep-bottomed platter CP is moved into a deep-bottomed small extra plate SP.

(7) In each mode described above, the information processing apparatus 10 is attached to the ceiling of the room LR; however, it is not limited to this. For example, the information processing apparatus 10 may be attached to the top surface of the dining table Tb. Alternatively, the information processing apparatus 10 may be installed outside the room LR. In a case in which the information processing apparatus 10 is installed outside the room LR, the information processing apparatus 10 communicates with the image capturing apparatus 90 via a network such as a mobile communication network or the Internet.

(8) In each mode described above, the information processing apparatus 10 is assumed to be a non-portable computer attached to the ceiling of the room LR; however, it is not limited to this, and it may be a portable terminal device such as a smart phone or a tablet terminal device.

(9) In each mode described above, the information processing apparatus 10 does not include the image capturing apparatus 90; however the information processing apparatus 10 may include the image capturing apparatus 90.

(10) The block diagrams used for description of each mode described above illustrate functional unit blocks. These functional blocks (components) are implemented by a freely selected hardware and/or software combination. There is no limitation on the means for implementing each functional block. In other words, each functional block may be implemented by one physically and/or logically combined device, or by two or more devices physically and/or logically separated and directly and/or indirectly connected (for example, by wire and/or wirelessly).

(11) The order of the processing procedures, sequences, flowcharts, and the like in each mode described above may be changed as long as no conflict occurs. For example, the method described in the specification presents various step elements in an exemplary order, but this is not limited to the presented specific order.

(12) In each mode described above, input and output information or the like may be stored in a specific location (for example, a memory) or a management table. The input and output information can be overwritten, updated, or written with additional information. The output information and the like may be deleted. The input information and the like may be transmitted to other devices.

(13) In each mode described above, the determination may be performed by a value (0 or 1) expressed as 1 bit, a Boolean value (true or false), or a comparison between numeric values (for example, a comparison with a predetermined value).

(14) In each mode described above, the storage device 30 is a recording medium readable by processor 20, for which a ROM and a RAM were given as examples, but it may be a flexible disc, a magnetooptical disk (for example, a compact disc, a digital versatile disc, or a Blu-ray (registered trademark) disc), a smart card, a flash memory device (for example, a card, a stick, or a key drive), a compact disc-ROM (CD-ROM), a register, a removable disk, a hard disk, a floppy (registered trademark) disk, a magnetic strip, a database, a server, or other appropriate storage media. The program may be transmitted from a network. Alternatively, the program may be transmitted from a communication network via an electronic communication line.

(15) Each mode described above may be applicable to systems using Long Term Evolution (LTE), LTE-advanced (LTE-A), SUPER 3G, IMT-Advanced, 4G, 5G, future radio access (FRA), W-CDMA (registered trademark), GSM (registered trademark), CDMA2000, ultra mobile broadband (UMB), IEEE 802.11 (Wi-Fi), IEEE 802.16 (WiMAX), IEEE 802.20, ultrawideband (UWB), Bluetooth (registered trademark), and other appropriate systems, and/or next-generation systems extended based on the system.

(16) In each mode described above, the information, signals, and the like described above may be represented using any of a variety of different technologies. For example, data, instructions, commands, information, signals, bits, symbols, chips, and the like that may be mentioned throughout the above description may be represented by voltage, current, electromagnetic waves, magnetic fields or particles, optical fields or photons, or a freely selected combination thereof. It should be noted that the terms described in this specification and/or terms necessary for understanding this specification may be replaced by terms having the same or similar meanings.

(17) Each function illustrated in FIG. 3 is implemented by any combination of hardware and software. Each function may be implemented by a single device, or may be implemented by two or more separate devices.

(18) The programs illustrated in each embodiment described above should be widely interpreted as an instruction, an instruction set, a code, a code segment, a program code, a subprogram, a software module, an application, a software application, a software package, a routine, a subroutine, an object, an executable file, an execution thread, a procedure, a function, or the like, regardless of whether it is called software, firmware, middleware, microcode, hardware description language, or other names.

Software, instructions, and the like may be transmitted and received via a transmission medium. For example, when the software is transmitted from a website, a server, or other remote sources using wired technology, such as a coaxial cable, fiber optic cable, twisted pair cable, or digital subscriber line (DSL), and/or wireless technology, such as infrared, wireless, or microwave technology, these wired and/or wireless technologies are included within the definition of the transmission medium.

(19) In each embodiment described above, information, parameters, and the like may be represented by absolute values, values relative to a predetermined value, or other corresponding information.

(20) The names used for the parameters described above are not limited in any way. Furthermore, the mathematical formulas and the like that use these parameters may differ from those explicitly disclosed herein.

(21) In each embodiment described above, the information processing apparatus 10 may be a mobile station. Those skilled in the art may refer to a mobile station as a subscriber station, mobile unit, subscriber unit, wireless unit, remote unit, mobile device, wireless device, wireless communicator, remote device, mobile subscriber station, access terminal, mobile terminal, wireless terminal, remote terminal, handset, user agent, mobile client, client, or other appropriate terms.

(22) In each embodiment described above, the phrase "based on" does not mean "based only on" unless otherwise explicitly stated. In other words, the phrase "based on" means both "based only on" and "based at least on."

(23) Any reference to an element using the designation "first", "second", or the like used herein does not generally limit the quantity or order of these elements. These designations may be used herein as a convenient way of distinguishing between two or more elements. Accordingly, references to the first and second elements do not mean that only two elements may be employed therein, or that the first element must precede the second element in any way.

(24) As long as the terms "including", "comprising", and variations thereof are used in each embodiment described above in the specification or in the claims, these terms are, like the term "comprising", intended to be inclusive. In addition, the term "or" used in the specification or in claims is not intended to be an exclusive OR.

(25) In the disclosure, for example, when articles such as "a", "an", and "the" in English are added in translation, these articles include plurals unless otherwise clearly indicated by the context.

(26) It is obvious to those skilled in the art that the present invention is not limited to the embodiments described in the specification. The present invention can be implemented in modified and altered modes without departing from the spirit and scope of the present invention defined in accordance with the claims. Therefore, the description of this specification is for illustrative purposes only and is not meant to be in any way limiting to the present invention. In addition, a plurality of modes selected from the modes illustrated the specification may be used in combination.

DESCRIPTION OF REFERENCE SIGNS

1 . . . dietary consumption estimating system, 10 . . . information processing apparatus, 20 . . . processor, 21 . . . acquirer, 22 . . . identification information generator, 23 . . . identifier, 24 . . . estimator, 25 . . . first determiner, 26 . . . second determiner, 28 . . . third determiner, 29 . . . consumption information generator, 30 . . . storage device, 90 . . . image capturing apparatus, CP . . . platter, FD . . . food, MI . . . video image information, P . . . still image, PI . . . image information, TO . . . tongs, U . . . person.

The invention claimed is:

1. An information processing apparatus comprising:
an acquirer configured to acquire video image information indicative of a video image obtained by photographically capturing a table, on which a vessel of a first type to serve food or beverage to be consumed by multiple people and a plurality of vessels of a second type in each of which a portion of the food or beverage is to be served are arranged, and the multiple people;
an identification information generator configured to generate, based on the video image information, first identification information for identifying each of the multiple people, second identification information for identifying each of the vessel of the first type and the plurality of vessels of the second type, and third identification information for identifying a type of the food or beverage;
an estimator configured to estimate, based on the video image information, an amount of food or beverage served in each of the vessel of the first type and the plurality of vessels of the second type;
a first determiner configured to determine, based on the video image information, whether an amount of food or beverage served in the vessel of the first type at a point in time of a determination is decreased compared to an amount of food or beverage served in the vessel of the first type at a point in time that is a predetermined period prior to the point in time of the determination;
a second determiner configured to, when a result of the determination by the first determiner is affirmative, determine, based on the video image information, whether food or beverage served in the vessel of the first type was consumed by one person of the multiple people, or the food or beverage was moved into one vessel of the plurality of vessels of the second type; and
a consumption information generator configured to, when a result of a determination by the second determiner indicates that food or beverage served in the vessel of the first type was consumed by the one person, generate consumption information in which an amount of food or beverage consumed by the one person, the one person, and the type of the food or beverage are associated with each other,
wherein the estimator is configured to, when the result of the determination by the second determiner indicates that the food or beverage was moved into the one vessel, increase the amount of the food or beverage served in the one vessel of the second type by an amount of decrease in food or beverage served in the vessel of the first type.

2. The information processing apparatus according to claim 1, further comprising:
an identifier configured to identify, based on the video image information, which of the multiple people each of the plurality of vessels of the second type corresponds to; and
a third determiner configured to determine whether an amount of food or beverage served in the one vessel of the plurality of vessels of the second type at a point in time of a determination is decreased compared to an amount of food or beverage served in the one vessel at a point in time that is the predetermined period prior to the point in time of the determination,
wherein the consumption information generator is configured to, when a result of a determination by the third determiner is affirmative, generate consumption information in which a person corresponding to the one vessel of the second type, an amount of food or beverage decreased from the food or beverage served in the one vessel at the point in time that is the predetermined period prior to the point in time of the determination by the third determiner, and the type of the food or beverage are associated with each other.

3. The information processing apparatus according to claim 2, wherein
the identifier is configured to:
  calculate a distance between the one vessel of the plurality of vessels of the second type and each of the multiple people; and
  identify a person positioned at a shortest distance among a plurality of distances calculated for the multiple people, as the person corresponding to the one vessel.

4. The information processing apparatus according to claim 1, wherein:
the video image information includes image information indicative of a still image for each of a plurality of frames; and
the estimator is configured to estimate the amount of food or beverage served in each of the vessel of the first type and the plurality of vessels of the second type based on a piece of image information indicative of a still image, in which neither the vessel of the first type nor the plurality of vessels of the second type are blocked by an object, among a plurality of pieces of image information corresponding to the plurality of frames, respectively.

5. The information processing apparatus according to claim 1, wherein:
the second determiner is configured to:
  start to track, when the result of the determination by the first determiner is affirmative, a destination of food or beverage served in the vessel of the first type based on the video image information;
  identify, based on the video image information, a person having a hand holding a utensil for moving food or beverage; and
  determine, when the food or beverage disappears without being moved into the plurality of vessels of the second type based on the video image information, the person having the hand holding the utensil as the one person who consumed the food or beverage served in the vessel of the first type.

6. The information processing apparatus according to claim 5, wherein
the second determiner is configured to:
calculate, based on the video image information, a distance between the hand holding the utensil and each of the multiple people; and
identify a person positioned at a shortest distance among a plurality of distances calculated for the multiple people, as the person having the hand holding the utensil.

* * * * *